United States Patent [19]

Noda et al.

[11] 4,410,546

[45] Oct. 18, 1983

[54] ANTIALLERGIC COMPOSITIONS

[75] Inventors: Kanji Noda, Chikushino; Akira Nakagawa, Tosu; Munehiko Hirano, Tosu; Kenji Yamagata, Tosu; Yoichi Nakashima, Tachiaraimachi; Terumi Hachiya, Chiyodamachi; Hiroyuki Ide, Fukuoka; Akihide Koda, Gifu, all of Japan

[73] Assignee: Hisamitsu Pharmaceutical Co., Inc., Tosu, Japan

[21] Appl. No.: 260,580

[22] Filed: May 5, 1981

[51] Int. Cl.³ ............................................. A61K 31/19
[52] U.S. Cl. .................................................... 424/317
[58] Field of Search ........................................ 424/317

[56] References Cited

U.S. PATENT DOCUMENTS 3,764,621 10/1973 Knowles ............................. 562/491

OTHER PUBLICATIONS

Chemical Abstracts 77:164084w (1972).
Chemical Abstracts 92:22815w (1980).

Primary Examiner—Leonard Schenkman
Attorney, Agent, or Firm—Jordan and Hamburg

[57] ABSTRACT

An antiallergic composition comprising, as the effective ingredient, a compound represented by the following general formula

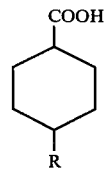

wherein R is n-butyl group or n-pentyl group, the compound being preferably supported by a carrier such as sugar, starch, gum arabic or calcium stearate.

2 Claims, No Drawings

ANTIALLERGIC COMPOSITIONS

This invention relates to a novel antiallergic composition and more particularly it relates to such an antiallergic composition comprising as the effective ingredient a compound represented by the following general formula (I)

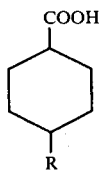  (I)

wherein R is n-butyl or n-pentyl group.

Glucocorticosteroids have heretofore been widely used as a medicine for remedy of allergic diseases such as allergic endocrinopathy, rheumatoid arthritis, collagen disease, allergic nephritis, allergic hemopathy, allergic digestive diseases, allergic hepatic trouble, dermatitis and bronchial asthma. However, such steroid preparations are very disadvantageous in that when they are habitually administered for a long period of time, they will, as side effects, induce or aggravate infectious diseases, cause various diseases due to anasarca and adrenal insufficiency and also cause gastrointestinal trouble, osteoporosis and the like. Thus, the habitual use of the steroid preparations is now considered undesirable and tends to be avoided.

In attempts to develop non-steroid type antiallergic substances which are efficacious for the above various diseases, the present inventors have synthesized various compounds and investigated the pharmacological actious thereof.

The said compounds represented by the general formula (I) have pharmacological actions such as hepatic function-improving action, anti-fibrinolytic action, anti-ulcerative action, immunity function hypo-reaction and normalization action, and they are useful as a hepatic function-improving agent, anti-fibrinolytic agent and anti-ulcerative agent and are also useful as a medicine for remedy of abnormal immunity function caused allergic diseases such as rheumatoid arthritis, autoimmunity diseases, asthma, allergic nephritis, allergic rhinitis, atopic dermatitis, gastroenteric allergy and anaphylaxis.

As is seen from the above, the antiallergic compositions of this invention are intended to mean not only a medicine having antiallergic actions in the narrow sense, but also a medicine having antiallergic actions including the aforesaid other various actions in the broad sense.

The compounds which are the effective ingredient of the antiallergic compositions of this invention and are represented by the aforementioned general formula (I), are crystalline by nature and may be prepared by a usual method to obtain therefrom capsules, granules, pills, powder, tablets, sirup, tincture, injections, siuppository, ointment, plaster, poultice, tape-carried preparations and the like. These preparations may be used both internally (orally) and externally.

Carriers usable in the said preparations include sugars such as glucose, saccharose, lactose, millet jelly and honey; cellulosic and starchy materials such as methylcellulose, crystalline cellulose, carboxymethylcellulose, hydroxypropylcellulose, corn starch and potato starch; and vegetable natural gum resins such as gum arabic and tragacanth gum. They further include powdered glycyrrhiza, rude extract of glycyrrhiza, powdered gentian, extract of gentian, dry yeast, extract of yeast, gelatine, powdered agar-agar, propylene glycol, glycerine, polyvinylpyrrolidone, sorbitol, water, alcohols, suspending agents, emulsifiers, surfactants, calcium stearate, magnesium stearate, methyl p-oxygenzoate, silicon and talc. These carriers may be used alone or in combination depending on the state and shape of preparations to be obtained, by employing a usually pharmaceutically allowable method.

The compounds of the formula (I) having antiallergic actions may be administered to human beings at a dose of 50–900 mg/day.

The compounds of the formula (I) which are the effective ingredient of the antiallergic compositions of this invention as indicated in the following Table 1, were described as being useful for certain purposes other than medicinal purposes in the literature "Z. Chem. 219 ('72)". In addition, these compounds of the formula (I) may be easily synthesized by the method disclosed in said literature.

TABLE 1

Effective ingredient of the composition of this invention, represented by the general formula (I)

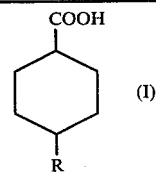 (I)

| Compound No. | Kind of geometrical isomer | R | Literature available |
|---|---|---|---|
| 1 | Trans | $(CH_2)_3CH_3$ | Z. Chem. 219 ('72) |
| 2 | Trans | $(CH_2)_4CH_3$ | Z. Chem. 219 ('72) |

The antiallergic actions exhibited by the antiallergic compositions of this invention will be substantiated by the following pharmacological experimants.

A. HOMOLOGOUS PASSIVE CUTANEOUS ANAPHYLAXIS (HOMOLOG. PCA) IN RATS

In accordance with the experimental method of Tada, T et al (J. Immunol., 106, 1002, 1971), a homologous passive cutaneous anaphylaxis (Homolog. PCA) reaction test was made on male Wistar strain rats, each weighing 160–170 g. In this test, DNP-As (Dinitrophenol coupled Ascaris suum extract) was obtained by reacting dinitrophenol (DNP) with protein extracted from Ascaris suum and was used as the antigen. Anti-DNP-As rats serum was prepaed using said antigen and was used as the antibody. This antibody exhibiting a sufficient titer was injected intradermally in an 0.1 ml dose into each of 3 sites on one side of the shaved back of each of rats, while the same dose of saline solution (physiological salt solution) was similarly injected into 3 sites on the other side thereof for comparison or to correct experimental errors if any. After the lapse of 48 hours, the test animals were each given 1.0 ml of the antigen solution (2.0 mg as the amount of protein) containing 0.25% Evans blue by intravenous injection thereinto. Thirty (30) minutes later, they were sacrificed by exsanguination and their skins were peeled to measure the area of PCA blueing lesion. The amounts of dye extravasated were each measured in accordance with the method proposed by Harada, M. et al (J. Pharm. Pharmacol., 23, 218, 1971).

The compounds of the formula (I) were orally administered at a dose of 200 mg/kg to the rats two hours prior to the administration of the antigen thereto. The test results are as shown in Table 2.

TABLE 2

| Test compound No. | Area of dye extravasated (mm²) | Inhibition rate (%) | Amount of dye extravasated (μg/site) | Inhibition rate (%) |
|---|---|---|---|---|
| Control | 99.11 ± 3.54 | — | 14.36 ± 0.83 | — |
| 1 | 76.87 ± 2.68 | 22.4 | 5.17 ± 0.32 | 64.0 |
| 2 | 67.20 ± 2.57 | 32.2 | 2.49 ± 0.29 | 82.7 |

B. REVERSED CUTANEOUS ANAPHYLAXIS TEST ON RATS

In accordance with Yamazaki et al's method (Folia Pharmacol. Jap. 60, §65, 1964) obtained by improving Ungar et al's method (Arch. intern. Pharmacodyn. 123, 71, 1959), male Wistar strain rats, each weighing about 100 g, were tested as follows.

First of all, anti-rat rabbit serum was dissolved in such an amount in an 0.5% solution of Evans blue as to obtain a 15% solution of the serum. The thus obtained serum solution was injected intradermally in an 0.05 ml dose into each of 2 sites on one side of the back of each of the rats, while an 0.5% solution of Evans blue in saline solution was also injected similarly in an 0.05 ml dose into each of 2 sites on one side of the back thereof. Two hours later, the test animals were sacrificed and their skins were peeled. The skins so peeled were punched as the indication of the Evans blue spot to separate the edema (swollen) portions thereof which were then measured for their weights.

The strength of intumescence was calculated from the following formula:

$$I (\%) = \frac{W_i - W_s}{W_s} \times 100$$

wherein $W_i$ is the weight of the inflammatory portion and $W_s$ is the weight of the control portion.

The antiallergic compounds of the formula (I) according to this invention were orally administered at a dose of 100 mg/kg to the rats one hour prior to the injection of the anti-rat rabbit serum. The test results are as shown in Table 3.

TABLE 3

| Test compound No. | Intumescence rate (%) | Inhibition rate (%) |
|---|---|---|
| Control | 42.58 ± 4.10 | — |
| 1 | 29.81 ± 7.17 | 30.0 |
| 2 | 25.00 ± 2.77 | 41.3 |

C. HISTAMINE RELEASE ON LUNG FRAGMENT OF GUINEA PIGS

The lungs of guinea pigs sensitized actively by ovalbumin were thoroughly irrigated by Tyrode's solution and then cut to obtain about 1-2 mm thick pieces. Two hundred (200) mg of the thus obtained fragments were accurately weighed out, immersed in Tyrode's solution and preincubated at 37° C. for 5 minutes. Then, the compounds of the formula (I) were each suspended in saline solution containing 0.5% of tragacanth gum, incubated at 37° C. for 20 minutes and induced by $10^{-6}$ g/ml of ovalbumin.

Following 20 minutes' incubation, the siolutin was chilled in ice and then measured for the amount of released histamine in the medium and remaining in the tissue by the use of fluorometric assay in accordance with the Shore et al's method (J. Pharmacol. exp. Ther. 127, 182, 1959). The test results are as shown in Table 4.

TABLE 4

| Test compound No. (sodium salt) | Inhibition rate (%) | |
|---|---|---|
| | Conc.: $10^{-4}$ g/ml | Conc.: $10^{-5}$ g/ml |
| 1 | 83.9 | 9.2 |
| 2 | 92.2 | 83.4 |

D. TEST FOR THE DEGRANULATION OF MESENTERIC MAST CELLS IN RATS

Rats were passively sensitized at their abdominal cavity by anti-DNP-As rat serum, 24 hours after which the mesenterium of the rats was enucleated. Then, 100 mg of the mesenterium were accurately weighed out, immersed in Tyrode's solution and preincubated at 37° C. for 5 minutes. Thereafter, the immersed solution was added to the antiallergic compounds of the formula (I) suspended in saline solution containing 0.5% of tragacanth gum, incubated at 37° C. for 20 minutes and then induced by $5 \times 10^{-6}$ g/ml of DNP-As. After 20 minutes' incubation, the solution was chilled in ice, and the mesenterium so reacted was dyed by the use of formalin (10% formaldehyde content) and an 0.1% tolwdine blue solution containing 0.1% of acetic acid, treated with ethanol and xylene and measured for degranulation by mirror inspection ($\times 4400$). The test results are as indicated in Table 5.

TABLE 5

| Test compound No. | Conc. (g/ml) | Degranulation rate (%) | Inhibition rate (%) |
|---|---|---|---|
| Control | | 97.11 ± 0.67 | |
| 1 | $10^{-4}$ | 71.45 ± 5.85 | 22.4 |
| 2 | $10^{-4}$ | 74.96 ± 2.91 | 18.6 |

E. ACUTE TOXITY TEST

The compounds (of the formula (I)) to be tested were each suspended in a saline solution containing 0.5% of tragacanth gum and then orally administered to 6 ddY strain mice in a group, each mouse weighing 20-25 g. LD$_{50}$ values were calculated from the death of mice in 3 weeks following the administration. The results are as shown in Table 6.

TABLE 6

| Test compound No. | LD$_{50}$ values (mg/kg) |
|---|---|
| 1 | >2000 |
| 2 | >2000 |

The compounds of the formula (I) according to this invention are not disclosed as to their use as a medicine, while they have been found by the present inventors to have remarkable pharmacological actions and safety as evidenced by the results of the aforementioned pharmacological tests and toxity tests and they are a very industrially useful medicine as an antiallergic agent.

This invention will be better understood by the following examples which illustrate the preparation of the antiallergic compositions containing the compounds of the formula (I) as the effective ingredient. In the examples, all the parts are by weight unless otherwise specified.

EXAMPLE 1

One hundred (100) parts of trans-4-n-butylcyclohexanecarboxylic acid which was the effective ingredient, 70 parts of granular lactose, 30 parts of corn starch (Japanese pharmacopoeis), 40 parts of crystalline cellulose (ditto) and 1.2 parts of magnesium stearate (ditto) were mixed together on a Shinagawa-type general-purpose mixer to obtain an antiallergic composition. The thus obtained composition was filled into No. 2 rigid capsules to obtain rigid capsules each enclosing therein 100 mg of the effective ingredient. The effective ingredient contained in the capsules exhibited remarkable antiallergic actions as indicated by the aforementioned experiments.

EXAMPLE 2

In this Example, 41.9 parts of trans-4-n-pentylcyclohexanecarboxylic acid which was the effective agent, 40.8 parts of lactose, 15.7 parts of potato starch and 1.6 parts of hydroxypropylcellulose were mixed together on a 10-liter stirring mixer to form a mixture which was incorporated with 50% ethanol and then kneaded together. The whole so kneaded was pelletized by an extrusion type pelleting machine, after which the resulting pellets were dried, pulverized and granulated to obtain granules. Then, 95.5 parts of the thus obtained granules were incorporated with 4 parts of sodium alginate and 0.5 parts of magnesium stearate were mixed together on said mixer to form a mixture which was tablated to obtain tablets each containing 40 mg of trans-4-n-pentylcyclohexanecarboxylic acid. The thus obtained tablets were clinically administered to asthmatic patients with the result that the patients were appreciated to be remarkably improving from their subjective symptoms and objective medical inspections.

As is apparent from the experiments and examples mentioned above, the effective ingredient of the antiallergic compositions of this invention exhibits inhibitive actions on homologous passive cutaneous anaphylaxis (Homolog. PCA), degranulation of mesenteric mast cells in rats and histamine release from lung fragments in guinea pig. The effective ingredient is a useful medicine for prophylaxis and remedy of allergic diseases and may be used for allergic diseases such as bronchial asthma, allergic rhinitis, allergic dermatitis, contact dermatitis, gastrointestinal allergy and anaphylaxis.

In addition, the effective ingredient is suggested to exhibit an anticomplementary action because of its inhibitive action on reversed cutaneous anaphylaxis (RCA) and it is also useful as a medicine for prophylaxis and remedy of cytolysis type diseases such as allergic hemolytic anemia, hypoleukocytosis, thrombocytopenia and other allergic hemopathics as well as of angiopathic troubles such as rheumatism, allergic nephritis and angitis.

What is claimed is:

1. An antiallergic composition comprising as a daily dose of the effective ingredient, 50–900 mg of a compound in the trans form represented by the following general formula (I)

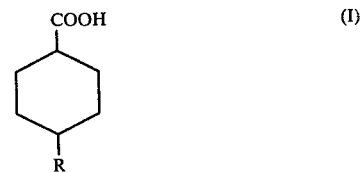

wherein R is n-butyl group or n-pentyl group, and a carrier material for mixing with the effective ingredient, said carrier material being at least one member selected from the group consisting of glucose, saccharose, lactose, millet jelly, honey, methylcellulose, hydroxypropylcellulose, corn starch, potato starch, gum arabic, tragacanth gum, powdered glycyrrhiza, rude extract of glycyrrhiza, powdered gentian, extract of gentian, dry yeast, extract of yeast, gelatine, powdered agar-agar, propylene glycol, glycerine, polyvinylpyrrolidone, sorbitol, suspending agents, emulsifiers, surfactants, calcium stearate, magnesium stearate, methyl p-oxybenzoate, silicon, talc, crystalline cellulose, carboxymethylcellulose and sodium alginate.

2. A method of treating a subject affected by allergies which comprises administering to said subject an antiallergic effective amount of an effective ingredient in the trans form represented by the following general formula (I)

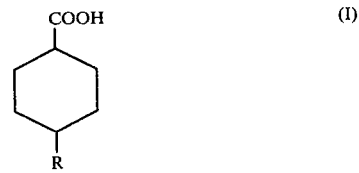

wherein R is n-butyl group or n-pentyl group, and a carrier material for mixing with the effective ingredient.

* * * * *